(12) United States Patent
Michel et al.

(10) Patent No.: US 8,348,960 B2
(45) Date of Patent: Jan. 8, 2013

(54) APPLICATOR FOR SUTURE/BUTTON CONSTRUCT

(75) Inventors: Gerlinde Michel, Munich (DE); Benedikt Bodinger, Machtenstein (DE); Karen L. Gallen, Naples, FL (US); Stephane Naudin, Planegg (DE)

(73) Assignee: Arthrex, Inc., Naples, FL (US)

( * ) Notice: Subject to any disclaimer, the term of this patent is extended or adjusted under 35 U.S.C. 154(b) by 1020 days.

(21) Appl. No.: 12/167,922

(22) Filed: Jul. 3, 2008

(65) Prior Publication Data

US 2009/0043318 A1 Feb. 12, 2009

Related U.S. Application Data

(60) Provisional application No. 60/949,453, filed on Jul. 12, 2007.

(51) Int. Cl.
*A61B 17/10* (2006.01)
(52) U.S. Cl. .................................................. 606/139
(58) Field of Classification Search .............. 606/74, 606/103, 139, 144, 145, 148, 232, 300
See application file for complete search history.

(56) References Cited

U.S. PATENT DOCUMENTS

| | | | |
|---|---|---|---|
| 5,211,647 A | 5/1993 | Schmieding | |
| 5,306,301 A | 4/1994 | Graf et al. | |
| 5,320,626 A | 6/1994 | Schmieding | |
| 5,645,588 A | 7/1997 | Graf et al. | |
| 5,665,112 A | 9/1997 | Thal | |
| 5,769,894 A | 6/1998 | Ferragamo | |
| 5,891,168 A | 4/1999 | Thal | |
| 5,921,986 A * | 7/1999 | Bonutti | 606/60 |
| 6,045,574 A | 4/2000 | Thal | |
| 6,056,752 A | 5/2000 | Roger | |
| 6,193,754 B1 | 2/2001 | Seedhom | |
| 6,517,578 B2 | 2/2003 | Hein | |
| 6,533,802 B2 | 3/2003 | Bojarski et al. | |
| 6,716,234 B2 | 4/2004 | Grafton et al. | |
| 7,235,091 B2 * | 6/2007 | Thornes | 606/232 |
| 7,455,683 B2 * | 11/2008 | Geissler et al. | 606/232 |
| 7,488,347 B1 * | 2/2009 | Goble et al. | 623/18.11 |
| 2003/0065361 A1 | 4/2003 | Dreyfuss | |
| 2004/0002734 A1 | 1/2004 | Fallin et al. | |
| 2004/0199166 A1 | 10/2004 | Schmieding et al. | |
| 2005/0033363 A1 | 2/2005 | Bojarski et al. | |
| 2005/0038427 A1 * | 2/2005 | Perriello et al. | 606/60 |
| 2005/0065533 A1 | 3/2005 | Magen et al. | |
| 2007/0179531 A1 | 8/2007 | Thornes | |
| 2008/0046009 A1 | 2/2008 | Albertorio et al. | |

FOREIGN PATENT DOCUMENTS

| | | |
|---|---|---|
| EP | 1 484 022 A2 | 12/2004 |
| EP | 1 504 773 A1 | 2/2005 |
| WO | WO 98/52471 | 11/1998 |
| WO | WO 2002/091959 | 11/2002 |

\* cited by examiner

*Primary Examiner* — Ryan Severson
*Assistant Examiner* — Jonathan W Miles
(74) *Attorney, Agent, or Firm* — Dickstein Shapiro LLP

(57) ABSTRACT

A technique for joint repair employing a suture/button construct and an applicator designed to securely engage a button of the suture/button construct. The button of the suture/button construct securely engages the shaft of the applicator. The suture from the button may be wrapped around a securing device (for example, a rod or bolt) located on or within the handle. The applicator with the secured button is introduced into the tissue (for example, soft tissue or a bone tunnel) and the button is passed through the tissue.

10 Claims, 12 Drawing Sheets

FIG. 4(b) DETAIL A

FIG. 4(c) DETAIL B

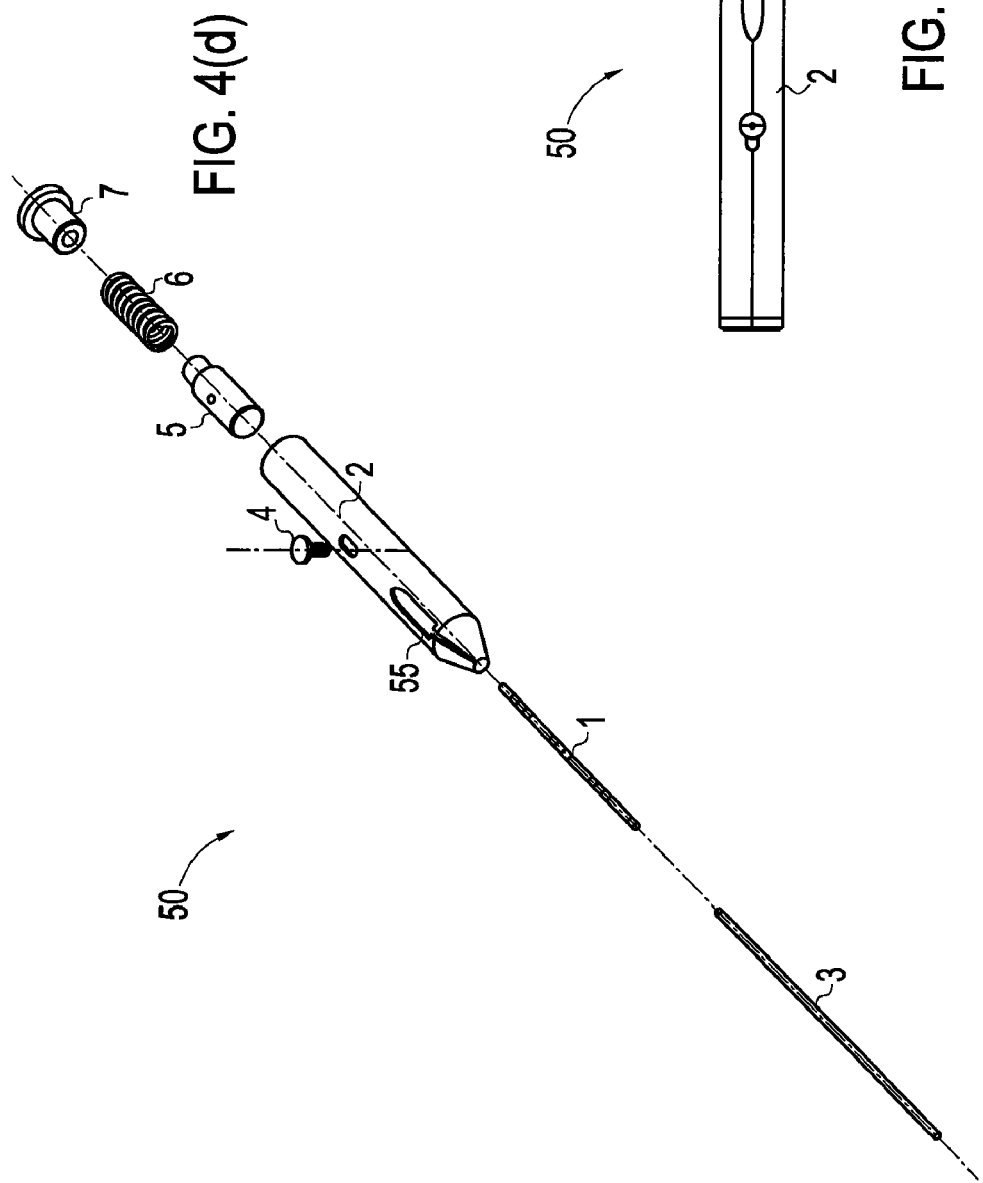

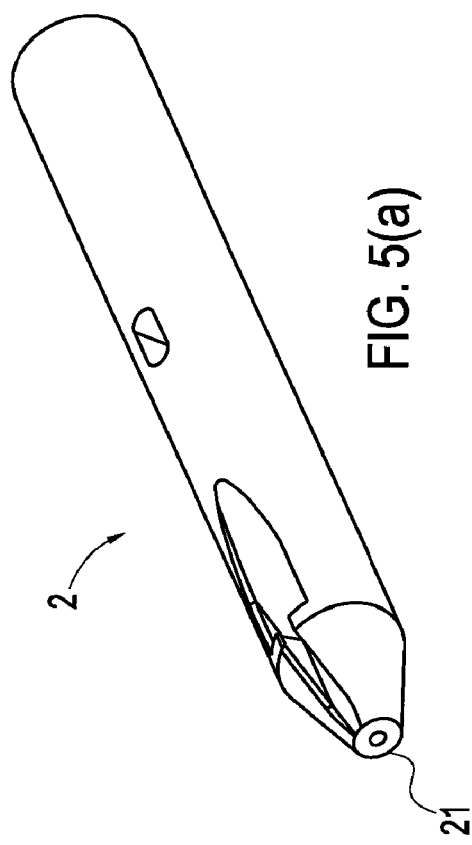
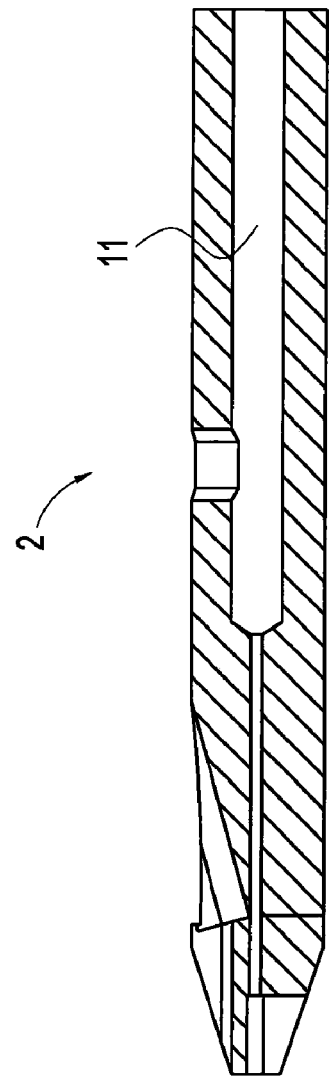
FIG. 5(a)
FIG. 5(b)

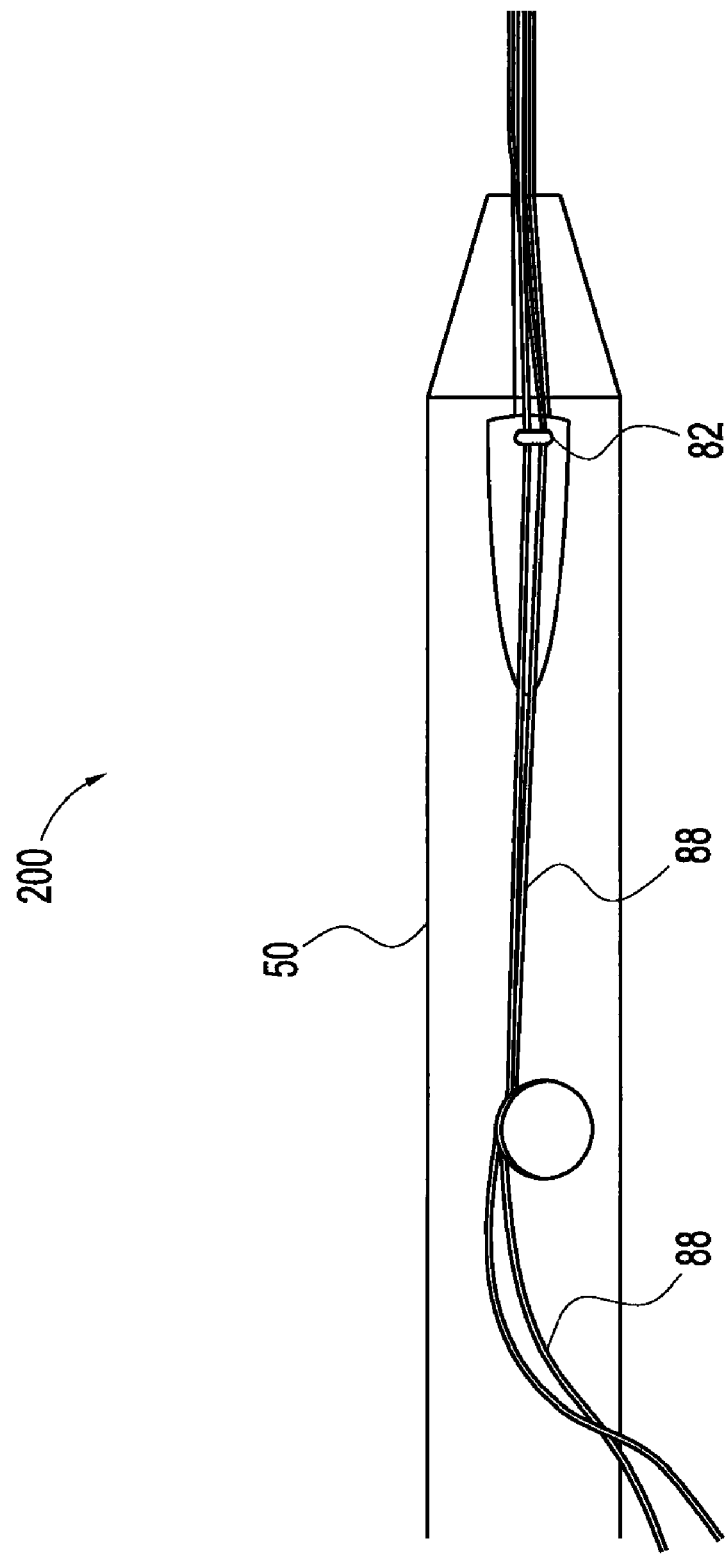

APPLICATOR FOR SUTURE/BUTTON CONSTRUCT

CROSS-REFERENCE TO RELATED APPLICATIONS

This application claims the benefit of U.S. Provisional Application No. 60/949,453, filed Jul. 12, 2007, the entire disclosure of which is incorporated by reference herein.

FIELD OF THE INVENTION

The present invention relates to the field of surgery and, more particularly, to an applicator for a suture/button construct in reconstructive surgeries.

BACKGROUND OF THE INVENTION

Suture-button constructs have been used for fixation of ankle syndesmosis (U.S. Pat. No. 7,235,091), acromioclavicular (AC) joint fixation (U.S. Patent Application Publication No. 2007/0179531) and more recently, for small joint surgery, such as bunion repair (U.S. Ser. No. 12/016,129, filed on Jan. 17, 2008), or lisfranc repair (U.S. Ser. No. 12/016,121, filed Jan. 17, 2008). In these small joint techniques, the suture-button construct is passed through a passage or tunnel (for example, a drilled hole) by employing a needle that pulls the button and the attached suture through the passage or tunnel. Pulling of the needle through the passage or tunnel, and subsequently out the skin, may be difficult, however, in certain circumstances, such as hallux valgus correction and lisfranc ligament repair. In addition, proper positioning of the buttons (for example, of the oblong and round button of the suture-button construct) may be difficult when the buttons are pulled through with suture and needle.

An instrument that would be able to push the buttons and attached suture through the drilled hole (instead of having to pull them through using the needle) is needed. Methods of advancing suture/button constructs through drilled tunnels or holes, particularly in situations where the needle and attached suture/button construct cannot be easily pulled through the hole and out the skin, are also needed.

BRIEF SUMMARY OF THE INVENTION

The present invention provides a technique and reconstruction system for surgical repairs. The system comprises an applicator designed for the manipulation and insertion of a suture/button construct (for example, a suture/button loop construct, or a construct with two buttons attached to a flexible strand) through tissue. The button of the suture/button construct is configured to securely engage the shaft of the applicator. The suture from the button may be wrapped around a securing device (for example, a rod or bolt) located on or within the handle. The applicator with the secured button is introduced into the tissue (for example, soft tissue or a bone tunnel) and the button is passed through the tissue.

A method of reconstructive surgery using a suture/button construct by employing an applicator of the invention comprises, for example, the steps of: (i) securing at least one button of a suture/button construct to an applicator; and (ii) passing the button through at least a portion of a tissue (for example, soft tissue or bone tunnel).

Other features and advantages of the present invention will become apparent from the following description of the invention which refers to the accompanying drawings.

BRIEF DESCRIPTION OF THE DRAWINGS

FIG. 11 illustrates an enlarged view of the handle of the loaded applicator of FIG. 10.

DETAILED DESCRIPTION OF THE INVENTION

Figure 1:
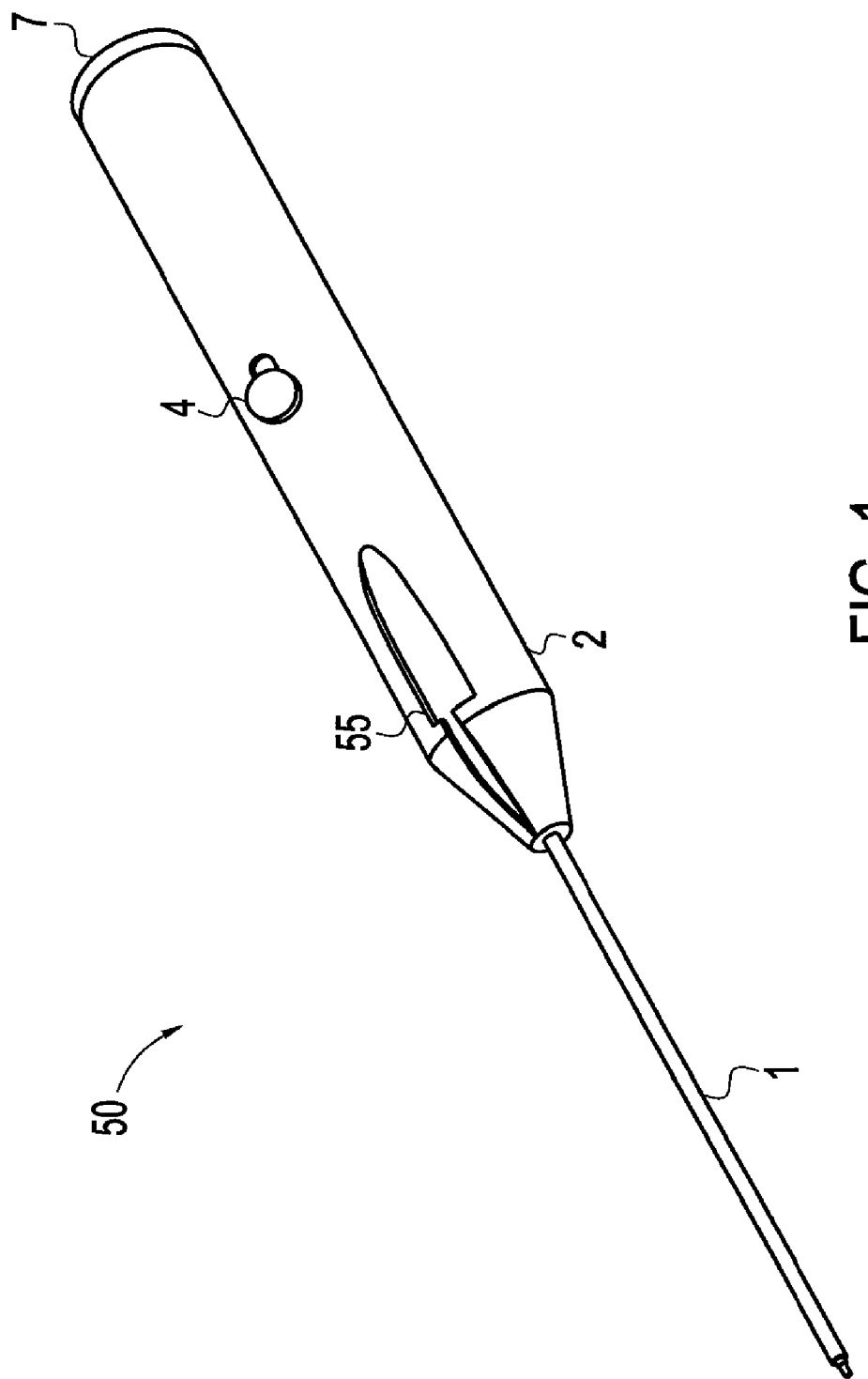
FIG. 1 illustrates a perspective view of the applicator according to the present invention.
Figure 2:
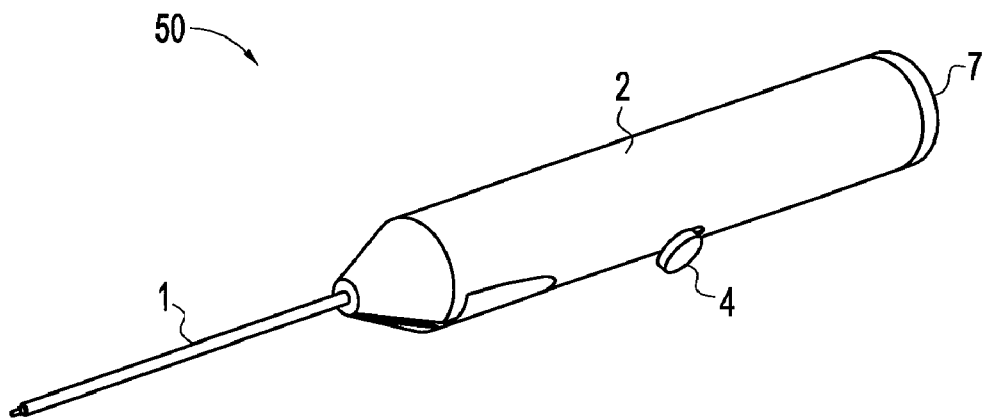
FIG. 2 illustrates another perspective view of the applicator according to the present invention.
Figure 3:
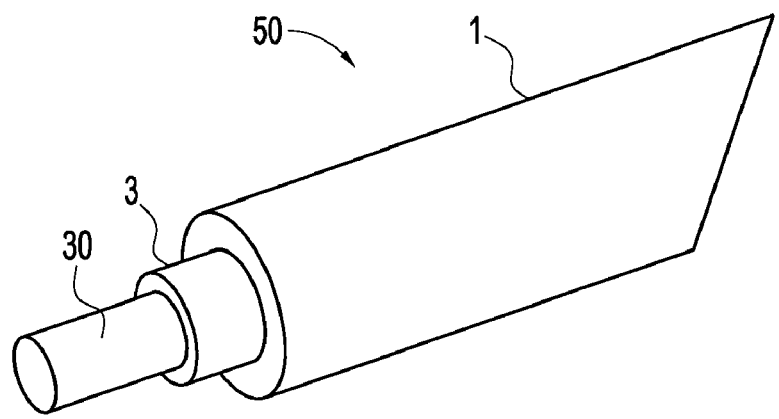
FIG. 3 is an enlarged view of the distal end of the applicator of FIG. 2.
Figure 4A:
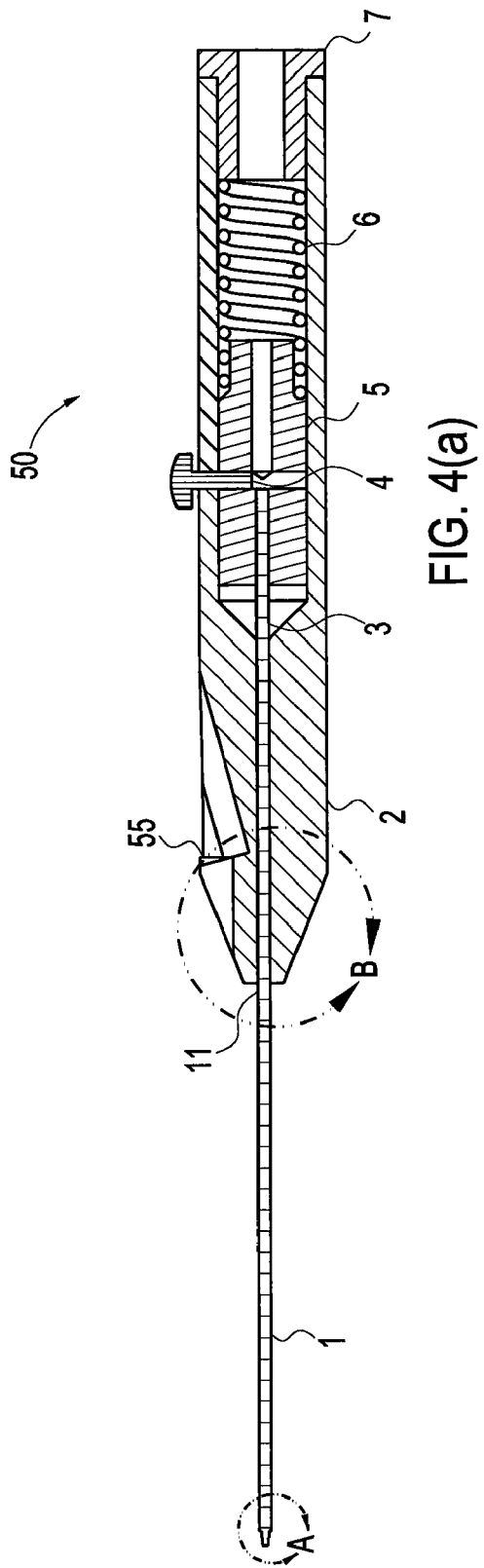
FIGS. 4(*a*)-(*e*) illustrate various views of the applicator of FIG. 2.
Figure 4A:
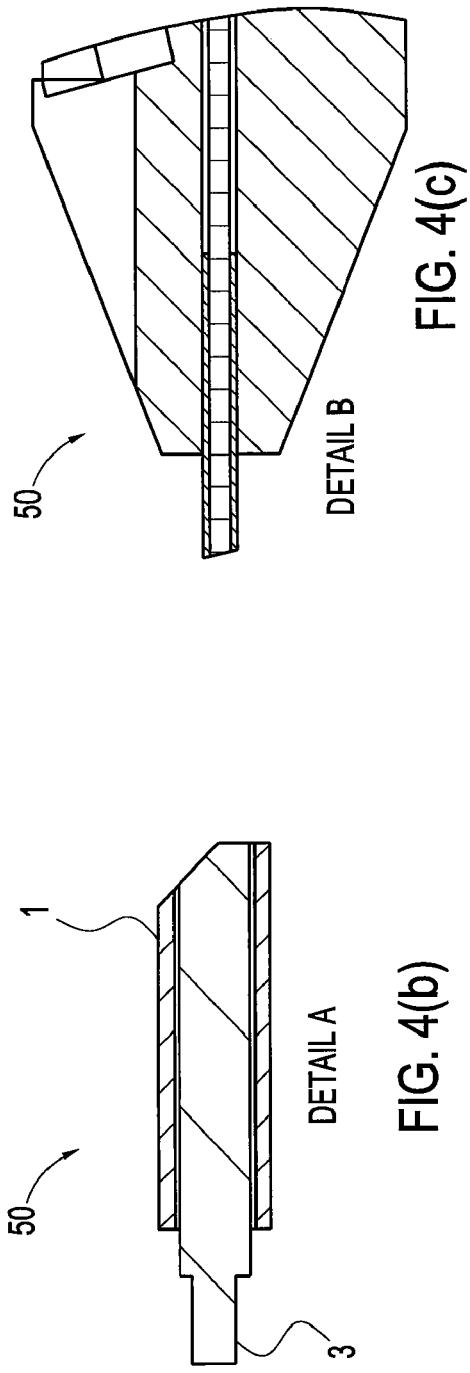
Figure 5C:
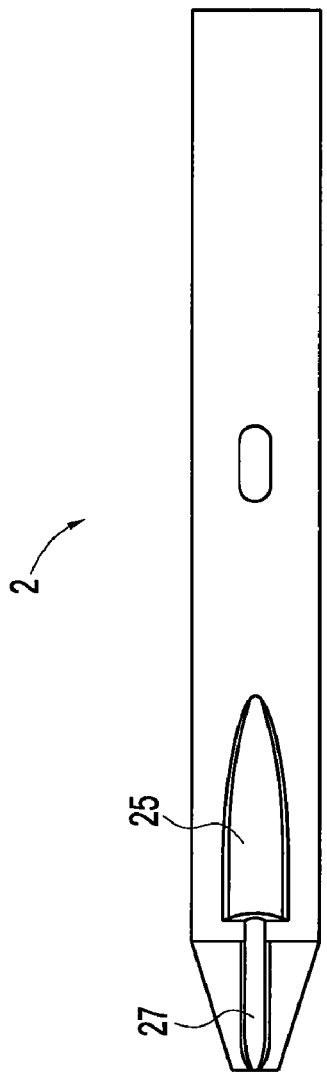
FIGS. 5(*a*)-(*d*) illustrate various views of the handle of the applicator of FIG. 1.
Figure 5D:
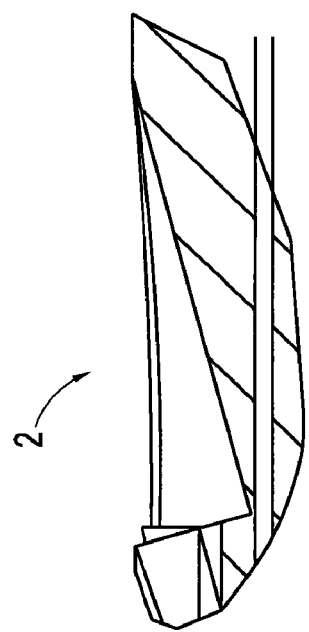
Figure 6A:
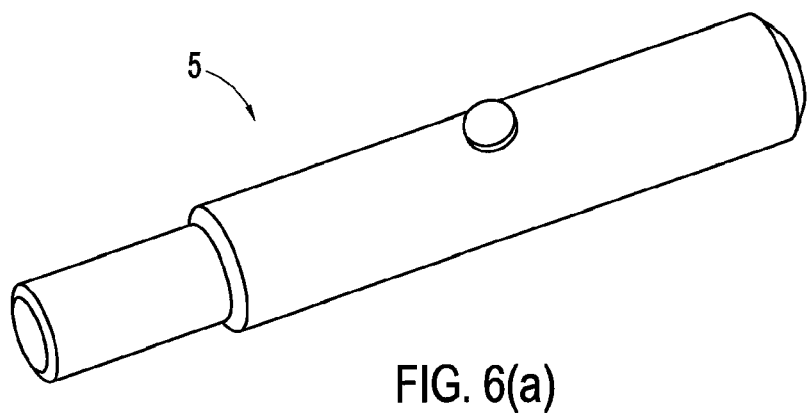
FIGS. 6(*a*)-(*c*) illustrate various views of the slide of the applicator of FIG. 1.
Figure 6B:
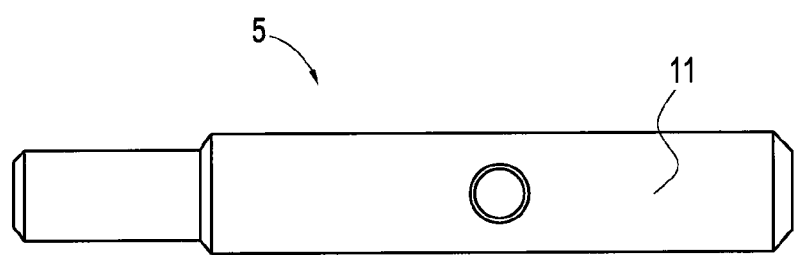
Figure 6C:
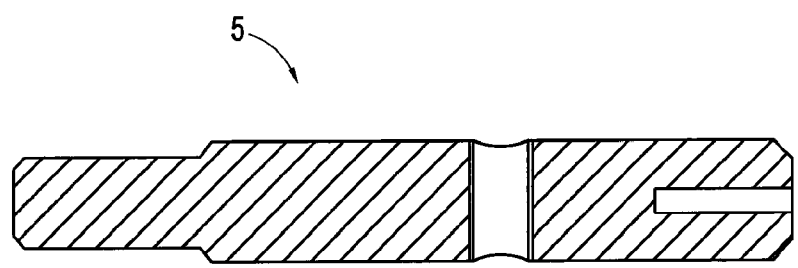

The present invention provides a technique and reconstruction system for surgical repairs. The system of the present invention comprises an applicator designed to secure a suture/button construct, to achieve strong suture button fixation on cortical bone. The applicator may be employed to manipulate and insert a suture/button construct (for example, a suture loop/button construct, or a construct with two buttons) through tissue (for example, soft tissue or bone).

The suture/button construct is loaded onto the applicator, on the end of a small diameter outer shaft. The suture/button construct is designed to securely engage the shaft of the applicator. In one embodiment, the button may be designed with a small recess (hole) on a side of the button, to accept the diameter of an inner shaft of the applicator. The button is placed at the most distal end of the applicator. In another embodiment, the button may be designed with a protrusion or protuberance that is configured to securely engage a corresponding recess in the shaft of the applicator. In this embodiment, the button is also placed at the most distal end of the applicator.

The suture from the button may be wrapped around a securing device (for example, a rod) located on or within the handle (for example, at about the middle of the handle). The applicator with the secured button is introduced into soft tissue or into a drilled hole in the bone, and passed through the soft tissue or bone hole.

If a multiple-button construct is employed, a first button (for example, an oblong button) may be designed with a small hole on the end of the button, to accept the diameter of an inner shaft of the applicator and to be placed at the tip of the applicator. A second button (for example, a round button) is placed inside a groove in the handle. The suture from the two buttons is wrapped around a securing device (for example, a rod) located on or within the handle. The applicator with the two buttons is introduced into tissue (for example, two drilled holes formed within two bones) and passed through the tissue (through the two holes). Once the second button is beyond the second bone, the inner shaft is advanced to release the button from the end of the device, thus allowing the first button to flip. In this manner, the buttons of the suture/button construct can be more accurately pushed into position and do not have to be pulled through with suture.

The present invention also provides a method of reconstructive surgery using a suture/button construct and an applicator designed to securely engage at least one button of the suture/button construct. The method of the present invention comprises, for example, the steps of: (i) securing at least one button of a suture/button construct to an applicator; and (ii) passing the button secured to the applicator through at least a portion of a tissue (for example, soft tissue or bone).

The present invention also provides a method of reconstructive surgery using a suture/button construct and a corresponding applicator by: (i) forming a bone tunnel or passage; (ii) securing at least one button of a suture/button construct to an applicator; (iii) passing the button secured to the applicator through the bone tunnel or passage; and (iv) securing the button to the bone cortex once the button exits the tunnel or passage.

Figure 9:
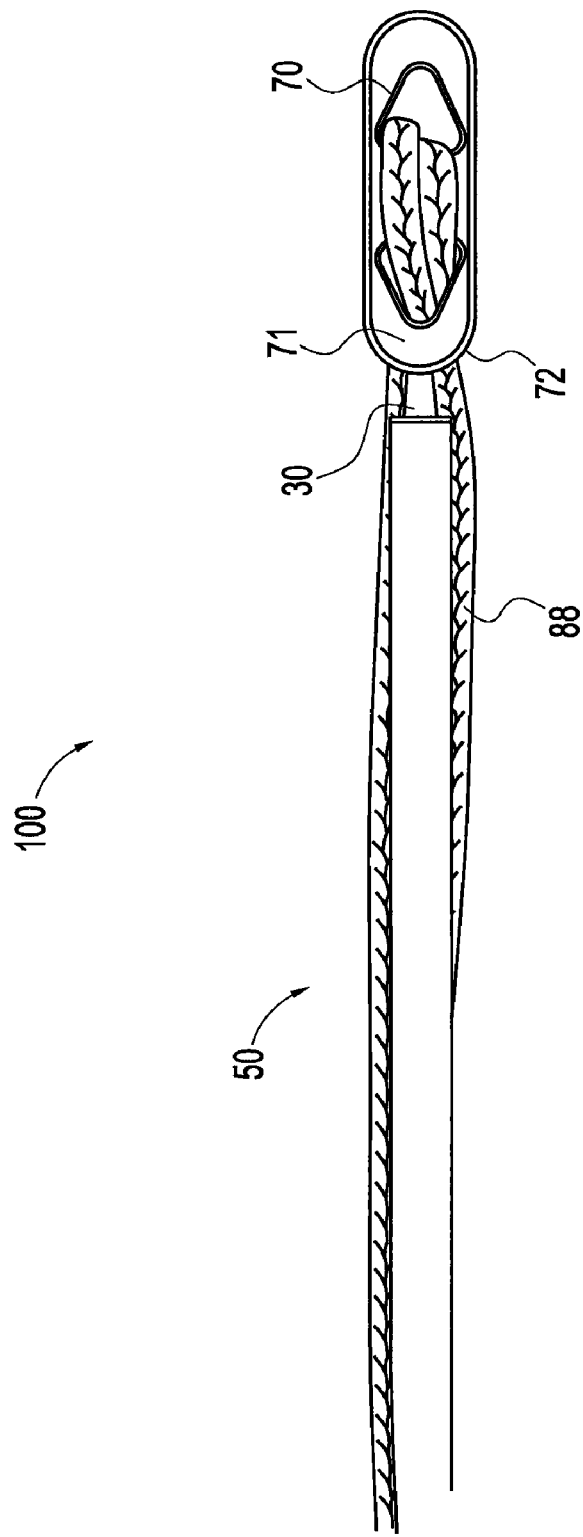
FIG. 9 illustrates the applicator of FIG. 1 loaded with one suture/button construct and according to a first embodiment of the present invention.
Figure 10:
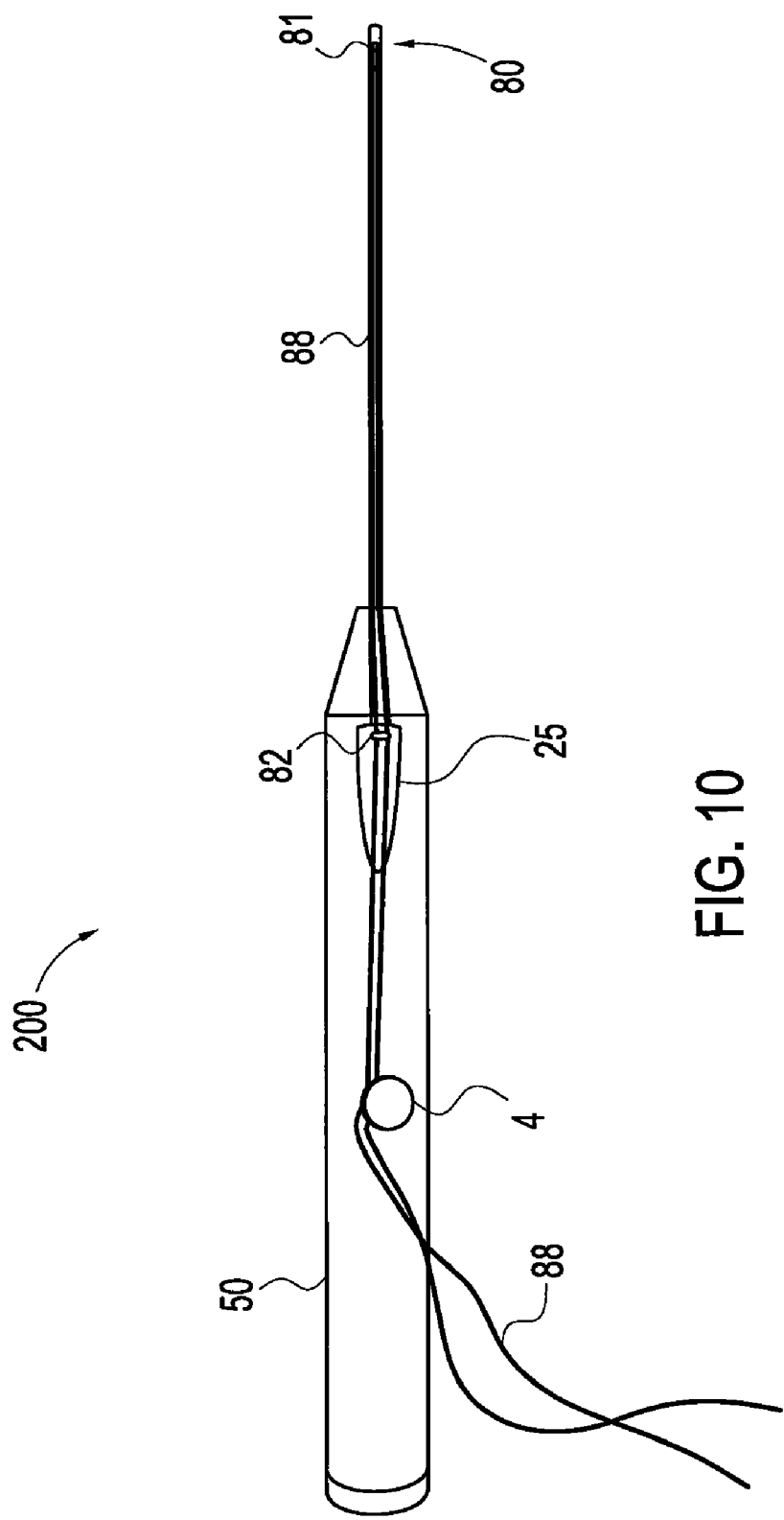
FIG. 10 illustrates the applicator of FIG. 1 loaded with two suture/button constructs and according to a second embodiment of the present invention.

Referring now to the drawings, where like elements are designated by like reference numerals, FIGS. 1-11 illustrate applicator 50 of the present invention designed to securely attach and engage a suture/button construct 70, 80. FIGS. 1-8 illustrate various views of the structural elements of applicator 50 of the present invention. FIG. 9 illustrates applicator 50 of FIGS. 1-8 loaded with suture/button construct 70, and according to one embodiment of the present invention. FIGS. 10 and 11 illustrate applicator 50 of FIGS. 1-8 loaded with suture/button construct 80 comprising two buttons (for example, a round button 82 and an oblong button 81) and according to another embodiment of the present invention.

As shown in FIGS. 1-8, applicator 50 of the present invention comprises a shaft 1 with a longitudinal axis 11, a handle 2, an inner rod 3, a rod or bolt 4 (designed to secure a strand of suture around it and to also retract the inner rod 3 to disengage the button of the suture/button constructs 70, 80), a slide 5, a spring 6 and a cap 7. Details of handle 2 of the applicator 50 are illustrated in FIGS. 5(a)-5(d). As shown in FIG. 5(c), groove 25 is provided within handle 2 to allow a button to rest within the groove, as detailed below. Groove 25 is in communication with longitudinal channel 27 having a diameter that is about half the diameter of groove 25. Channel 27 extends from groove 25 to about a most distal surface 21 of handle 2. Preferably, channel 27 has a width about equal to the width of a button resting within groove 25.

Handle 2 of applicator 50 may be provided with an outer surface with a grip formed of alternating raised edges and depressions. In this manner, a surgeon holding the handle can firmly grasp the instrument and can easily access and manipulate the suture/button construct.

Shaft 1 of applicator 50 is provided with an engagement mechanism 30 that is designed to securely engage a corresponding structure (for example, a cavity) of at least one of the buttons of suture/button construct 70, 80. For example, and as more clearly illustrated in FIG. 3, inner rod 3 (which is housed by shaft 1) is provided with a smaller diameter shaft 30 designed to accept and securely engage a recess or cavity formed within the body of one of the button of the suture/button construct 70, 80 (for example, button 71 of suture/button construct 70). The cavity of the button preferably has a diameter about equal to the diameter of the smaller diameter shaft 30 to allow a tight fit of the button to the applicator during advancement of the button through soft tissue or bone hole.

FIG. 9 illustrates assembly 100 comprising applicator 50 securely engaging button 71 of suture/button construct 70. Smaller diameter shaft 30 of applicator 50 securely engages hole 72 provided laterally within the body of button 71, to allow the suture/button construct 70 to orient longitudinally (i.e., parallel to the longitudinal axis 11 of the applicator 50) for insertion within tissue (for example, within a drilled hole or socket). In other embodiments, however, the engagement mechanism may constitute of shaft 30 of applicator 50 provided with a recess designed to receive a corresponding protuberance of button 71.

Figure 7B:
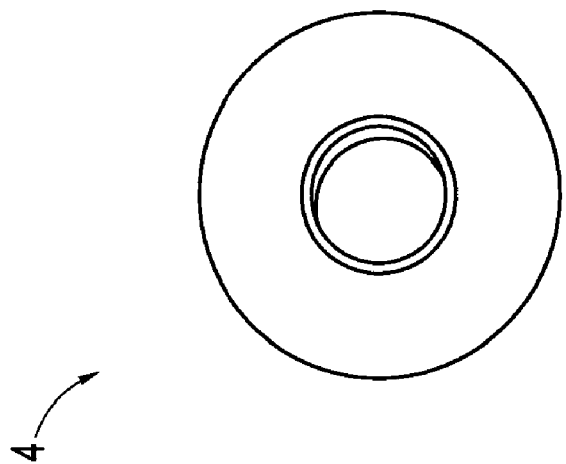
FIGS. 7(*a*)-(*b*) illustrate various views of the bolt of the applicator of FIG. 1.
Figure 7A:
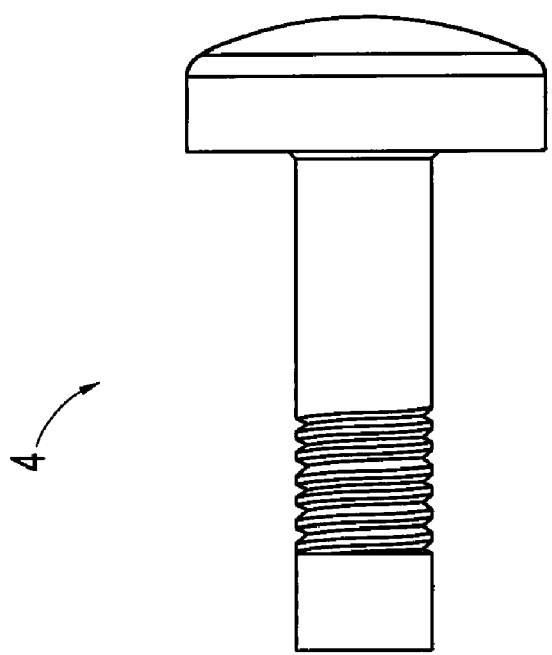
Figure 8C:
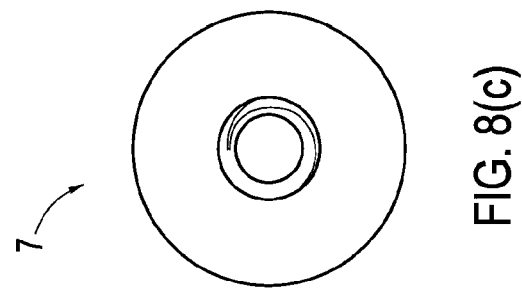
FIGS. 8(*a*)-(*c*) illustrate various views of the cap of the applicator of FIG. 1.
Figure 8A:
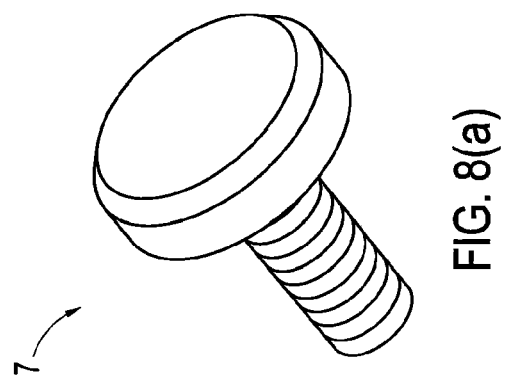
Figure 8B:
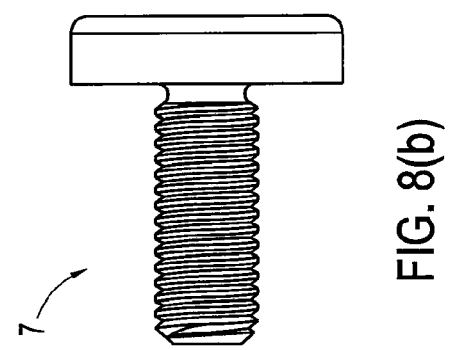

As shown in FIG. 7, a securing device 4 is provided within or on the handle 2 of applicator 50. The securing device may comprise a rod or bolt 4 and may be located at about the middle of the handle 2. The securing device allows a strand of flexible material (for example, a suture strand) to wrap around it to enhance the engagement of the button to the applicator shaft. For example, FIG. 10 illustrates suture 88 of the suture/button construct 80 wrapped around rod or bolt 4 of FIGS. 1, 2 and 7, located at about the middle of handle 2. Securing device 4 is also used to retract the inner rod 3 to disengage the button of the suture/button constructs 70, 80.

FIGS. 10 and 11 illustrate assembly 200 comprising applicator 50 of FIGS. 1-8 loaded with a suture/button construct 80 having at least two buttons (for example, an oblong button 81 and a round button 82) and according to another embodiment of the present invention. In this embodiment, the oblong button 81 may be designed with a small hole 72 on the end of the button (as in the previous embodiment), to accept the diameter of the inner shaft of the applicator 50 and to be placed at the tip of the applicator 50. The round button 82 may be placed inside groove 25 in the handle 2. The suture 88 from the two buttons 81, 82 is wrapped around securing device 4 (for example, rod or bolt 4) located at about the middle of the handle. In this manner, securing suture 88 to post 4 of the applicator allows the first button 81 to be oriented about parallel to the longitudinal axis 11 of the device, while the second button 82 is oriented about perpendicular to the longitudinal axis 11 of the device. Assembly 200 formed by applicator 50 with the two buttons 81, 82 is next introduced into drilled holes in the bones and passed through the bones.

Once the round button 82 abuts the second bone (i.e., it is in contact with the bone cortex), the inner shaft is advanced to release the oblong button 81 from the end of the device, thus allowing the button 81 to flip. In this manner, buttons 81, 82 of the suture/button construct 80 can be more accurately pushed into position and do not have to be pulled through with suture. In exemplary embodiments, the buttons 81, 82 of the suture/button construct 80 are attached by a high-strength suture, forming a suture-button assembly 200) and are successfully employed in fixation techniques for corrections of the metatarsal angle. In these methods, the buttons with the attached suture are passed through a passage or tunnel (for example, a drilled hole) not by employing a needle that pulls the buttons and the attached suture through the passage or tunnel, but rather by pushing the buttons with the applicator 50 of the present invention. In this manner, pulling of the needle through the passage or tunnel, and subsequently out the skin (which is difficult in hallux valgus correction and lisfranc ligament repair) is eliminated. In addition, the positioning of the buttons (for example, of the oblong and round buttons 81, 82 of the construct) is enhanced since the buttons are pushed in a forward motion rather than being pulled through with suture and needle.

The buttons of the suture/button constructs 70, 80 of the present invention (such as buttons 71, 81 and 82) are preferably formed of stainless steel, titanium alloy, titanium, PEEK or PLLA, among others. As shown in the drawings, the buttons may have an oblong configuration and a width that is preferably less than about 1 mm narrower than the width of the drill hole through which the button is inserted and subsequently passed through. The buttons are provided with one or more inside eyelets that allow the passage of the suture 88.

Preferably, button 71 has a length of about 10 mm to about 20 mm, more preferably of about 12 mm to about 15 mm, and a width that is less than about 1 mm narrower than the width of the drill hole through which the button is inserted and subsequently passed through. Preferably, button 71 is very small, having a width that allows it to pass through a 3 mm cortical pin hole without over drilling, which in turn saves time and preserves bone.

In an exemplary embodiment, suture 88 of the suture/button constructs of the present invention may be a single high strength suture such as FiberWire® suture, sold by Arthrex, Inc. of Naples, Fla., and described in U.S. Pat. No. 6,716,234, the disclosure of which is incorporated by reference herein. The suture may be available in various lengths, diameters, colors or combinations of colors.

The system of the present invention may be employed for fixation of bone to bone, or for fixation of soft tissue to bone. In an exemplary embodiment, assembly 100 (comprising applicator 50 and suture/button construct 70) of the present invention may be used to secure a soft tissue graft in a bone socket in a retrograde manner, for example. According to another exemplary embodiment, assembly 100 of the present invention may be used to secure a bone-to-bone (BTB) graft in a femoral tunnel or socket in a retrograde manner, for example. In a particular and only exemplary embodiment, a method of reconstructive surgery using a suture/button construct and a corresponding applicator comprises, for example, the steps of: (i) forming a bone tunnel or socket in an antegrade or a retrograde manner (using a cutter which is inserted in a retrograde manner through the bone); (ii) securing a graft (soft tissue graft or BTB graft) to the suture/button construct 70; (iii) securing the button of a suture/button construct 70 to applicator 50; (iv) passing the button secured to the applicator 50 through the bone tunnel or socket; and (v) securing the button to the bone cortex once the button exits the tunnel or socket.

According to one embodiment of the present invention, the bone tunnel or socket is a femoral socket prepared by employing a retrograde drilling device provided with a cutter detachable from a guide pin, in the manner described in U.S. Patent Application Publication No. 2004/01990166, entitled "ACL Reconstruction Technique Using Retrodrill," the disclosure of which is hereby incorporated by reference herein in its entirety.

According to yet another exemplary embodiment, assembly 200 of the present invention (comprising applicator 50 and suture/button construct 80 with two buttons 81, 82) may be used for corrections of the metatarsal angle, for hallux valgus corrections and/or lisfranc ligament repair. In a particular and only exemplary embodiment, a method of correcting the metatarsal angle using the assembly 200 of the present invention comprises, for example, the steps of: (i) forming a first tunnel or socket through a first metatarsal or through a cuneiform; (ii) forming a second tunnel or socket through a second metatarsal; (iii) providing assembly 200 of the present invention (comprising applicator 50 and the suture/button construct 80 with the two buttons 81, 82 loaded thereon) in the vicinity of the first and second tunnels; (iv) passing the oblong button through the first and second tunnels; and (v) securing the buttons to the cortex of each of the first and second metatarsals or of the cuneiform, to reduce the intermetatarsal space.

Although the present invention has been described in connection with preferred embodiments, many modifications and variations will become apparent to those skilled in the art. While preferred embodiments of the invention have been described and illustrated above, it should be understood that these are exemplary of the invention and are not to be considered as limiting. Accordingly, it is not intended that the present invention be limited to the illustrated embodiments, but only by the appended claims.

What is claimed as new and desired to be protected by Letters Patent of the United States is:

1. A method of positioning tissue within the body, comprising the steps of:
    providing a suture/button construct having an oblong button with at least one eyelet and a flexible suture strand attached to the at least one eyelet;
    attaching the tissue to be positioned to the suture/button construct;
    providing an instrument for attaching and engaging the suture button construct, the instrument comprising a handle, a shaft with a distal end, an inner rod movable within the shaft and having a distal end positionable to extend beyond the distal end of the shaft, and a securing mechanism;
    engaging the oblong button of the suture/button construct to the distal end of the inner rod extending beyond the distal end of the shaft of the instrument by inserting the distal end of the inner rod into a corresponding recess provided in an end of the oblong button, so that the oblong button extends outwardly from the distal end of the shaft in longitudinal alignment with the shaft;
    securing the flexible suture strand to the securing mechanism of the instrument; and
    advancing the instrument with the suture/button construct through a socket or tunnel in a bone.

2. The method of claim 1 further comprising the steps of:
    pushing the suture/button construct with the attached tissue through the socket or the tunnel in the bone;
    positioning the attached tissue within the socket or the tunnel in the bone; and
    retracting the inner rod to disengage the oblong button from the instrument and securing the oblong button on a surface of the bone.

3. The method of claim 1, wherein the tissue to be positioned is biological or non-biological tissue.

4. The method of claim 1, wherein the tissue to be positioned is selected from the group consisting of ligament, tendon, bone and cartilage.

5. The method of claim 1, wherein the tissue to be positioned is soft tissue graft or BTB graft.

6. A method of surgery, comprising the steps of:
    forming a bone tunnel or socket;
    providing a suture loop/button construct in the vicinity of the bone tunnel or socket, the suture loop/button construct comprising an oblong button and a round button, each of the oblong and round buttons having at least one eyelet, and a suture loop attached to the at least one eyelet of the oblong and round buttons;
    providing an instrument in the vicinity of the suture/button construct, the instrument comprising a shaft having a proximal end and a distal end, an inner rod movable within the shaft and having a distal end positionable to extend beyond the distal end of the shaft, and a handle located at the proximal end;
    securing the oblong button to a most distal region of the distal end of the inner rod extending beyond the distal end of the shaft of the instrument by inserting the distal end of the inner rod into a corresponding recess provided in an end of the oblong button, so that the oblong button extends outwardly from the distal end of the shaft in longitudinal alignment with the shaft;

positioning the round button within a groove in the handle; and advancing the oblong button through the bone tunnel or socket while secured to the distal end of the inner rod.

7. The method of claim 6 further comprising the step of passing the oblong button through the bone tunnel or socket, retracting the inner rod to disengage the oblong button from the instrument, and securing the oblong button to a bone cortex abutting the bone tunnel or socket.

8. The method of claim 6 further comprising the step of securing the round button to another bone cortex abutting the bone tunnel or socket.

9. A method of, surgery comprising the steps of:

forming a bone tunnel or socket;

providing a suture loop/button construct in the vicinity of the bone tunnel or socket, the suture loop/button construct comprising an oblong button having at least one eyelet, and a suture loop that is attached to the at least one eyelet;

attaching a graft to the suture loop/button construct;

engaging the suture loop/button construct to an instrument, the instrument having a shaft with a distal end and an inner rod movable within the shaft and having a distal end positionable to extend beyond the distal end of the shaft, the suture loop button construct being engaged to the instrument by inserting the distal end of the inner rod into a corresponding recess provided in an end of the oblong button, so that the oblong button extends outwardly from the distal end of the shaft in longitudinal alignment with the shaft;

advancing the instrument and the engaged suture loop/button construct attached to the graft through the bone tunnel or socket; and subsequently securing the graft within the bone tunnel or socket by retracting the inner rod to disengage the oblong button from the instrument and securing the oblong button to a surface of the bone tunnel or socket.

10. The method of claim 9, wherein the bone tunnel or socket is formed in a retrograde manner using a rotary drill cutter.

* * * * *